(12) United States Patent
Friedman

(10) Patent No.: US 6,450,170 B1
(45) Date of Patent: *Sep. 17, 2002

(54) TREATMENT OF MIGRAINE, POST-TRAUMATIC HEADACHE, TENSION-TYPE HEADACHES, ATYPICAL FACIAL PAIN, CERVICAL PAIN AND MUSCLE SPASM

(76) Inventor: Mark Friedman, 5 Forest Ct., Larchmont, NY (US) 10538

( * ) Notice: Subject to any disclaimer, the term of this patent is extended or adjusted under 35 U.S.C. 154(b) by 16 days.

This patent is subject to a terminal disclaimer.

(21) Appl. No.: 09/595,375

(22) Filed: Jun. 15, 2000

(51) Int. Cl.$^7$ ................................................ A61B 19/00
(52) U.S. Cl. .............................. 128/898; 606/1; 607/88; 607/89
(58) Field of Search ..................... 607/88–95; 606/3; 128/898

(56) References Cited

U.S. PATENT DOCUMENTS

| | | | | |
|---|---|---|---|---|
| 5,514,168 A | * | 5/1996 | Friedman | 607/89 |
| 5,640,978 A | * | 6/1997 | Wong | 128/898 |
| 6,139,861 A | * | 10/2000 | Friedman | 424/435 |

* cited by examiner

Primary Examiner—Linda C. M. Dvorak
Assistant Examiner—Ahmed Farah
(74) Attorney, Agent, or Firm—Evelyn M. Sommer

(57) ABSTRACT

A new method of treatment of migraine, tension-type headaches, post-traumatic headache, atypical facial pain as well as cervical pain and muscle spasm is presented, comprising the application of bursts of low power laser light to the area of intra-oral tenderness associated with the above conditions. The zone of tenderness is in the area of the plexus formed by the posterior and middle superior alveolar branches of the ipsilateral maxillary nerve. The intra-oral tenderness associated with migraine, tension-type headaches, post-traumatic headache, atypical facial pain, cervical pain and muscle spasm disappears almost immediately, returning in approximately 3 hours to a few days, With repeated applications, a marked decrease or elimination of the intra-oral tenderness and similar elimination of migraine, tension-type headaches, post-traumatic headache, atypical facial pain, cervical and muscle spasm frequency and intensity was observed. The brief application of bursts of low power laser light (non-cutting 5–60 mW) from a low power Helium-Neon, Gallium Arsenide or Gallium Aluminum Arsenide laser, having a maximum output of 60 mW ,typically utilizing an application time of 2–15 minutes.

16 Claims, 4 Drawing Sheets

TREATMENT OF MIGRAINE, POST-TRAUMATIC HEADACHE, TENSION-TYPE HEADACHES, ATYPICAL FACIAL PAIN, CERVICAL PAIN AND MUSCLE SPASM

BACKGROUND OF THE INVENTION

The present invention relates to a new method for the treatment of migraine, tension-type headaches, atypical facial pain, post-traumatic headache, cervical pain and muscle spasm.

In accordance with the invention, the method of treatment for these headaches, atypical facial pain, cervical pain and muscle spasm comprises the application of low power laser light to the area of intra-oral tenderness which has been found by the inventor herein to be associated with the aforesaid conditions. This zone of tenderness and an increased local temperature are in the area of the plexus formed by the posterior superior alveolar branch of the ipsilateral maxillary nerve. The zone of tenderness is located bilaterally when the symptoms are bilateral and unilaterally when the symptoms are one sided.

In the case of tension (muscle contraction) headaches in the frontalis or forehead and/or orbital region, the laser emitted radiation can also be applied to the supraorbital nerve as it emerges from the supraorbital notch or foramen over the eye or at the infraorbital foramen beneath the eye, or at the mandibular foramen in the mandible This laser application is performed either separately or in conjunction with the laser treatment directed to the area of intra-oral tenderness. The intra-oral tenderness associated with migraine, tension-type headaches, post-traumatic headache, cervical muscle spasm and atypical facial pain is markedly decreased or disappears immediately after intra-oral laser application, returning in approximately three hours to a few days, but most importantly it has been found that with repeated applications, the tenderness returns to a lesser degree along with a decrease in symptoms. For the above-noted conditions, a marked decrease or elimination of the above noted conditions' frequency and intensity takes place. Immediate relief is often noted when the patient is symptomatic.

In practicing the method of the invention, low level lasers of several types were used including Helium-Neon lasers emitting light at 632.8 nm, and Gallium Arsenide diode lasers emitting light at 635 nm and Gallium Aluminum Arsenide diode lasers emitting light at 830 nm. It is also possible to use a combination of different types of low level emitting lasers simultaneously; i.e., Helium-Neon and Gallium Aluminum Arsenide, or other low-level use lasers such as a $CO_2$ infrared laser.

Headaches can be classified into three main groups: vascular such as migraine or cluster, tension or muscle contraction and traction and inflammatory headaches. The latter group may be caused by stroke, hypertension, hemorrhage from an aneurysm, brain tumor, infections or inflammation.

Migraine is the most common type of headache causing patients to consult a physician. According to the American Council for Headache Education, migraine type headache is reported to occur in 18% of females and 6% of males in the United States. Considering this incidence, the economics of migraine, time lost from work, inefficiency etc., is substantial. Effective treatment can increase the patient's ability to live a normal and productive life. In addition to pain, the symptoms most commonly associated with migraine include nausea and vomiting, photophobia, phonophobia, pallor, and a desire to lie down.

Multiple humoral agents have been postulated as being the major factor in migraine. These include serotonin, histamine, prostaglandins, platelet factors, endorphins, substance P, and bradykinea. Low power density lasers have been shown to act on prostaglandin (PG) synthesis, increasing the change of PGG2 and PGH2 into PG12. These products are known to have an anti-inflammatory action. The etiology of migraine has been studied by many investigators. Research has implicated the meninges as the source for vascular head pain, as an unknown trigger activates perivascular trigeminal axons which release vasoactive neuropeptides (substance P, calcitonin gene-related peptide, histamine, bradykinin, prostaglandins etc.). These agents produce a local sterile inflammation, causing transmission of nociceptive impulses to the brain stem and higher centers, for the registration of head pain (Moskowitz MA, Trends in Pharmacological Sciences, August 1992. The intra-oral zone of tenderness located in the area of the root apices of the maxillary molars appears to be increased, with subsequent local swelling. The swelling exerts pressure on the maxillary nerve, resulting in trigeminal axonal activation. In the presence of this lowered threshold, various other triggers can cause the headache, for example, hormones, wine, chocolate, changing weather fronts, etc.

Migraine therapy is either prophylactic or symptomatic. Prophylactic medication may be selected for a patient with 2–4 headaches per month, if they are severe enough to interfere with daily activities. Beta blockers such as propranolol (Inderal) are the most common. Other medications, often used, are serotonin antagonists such as methysergide maleate (Sansert), calcium channel blockers (Verapamil), amitriptyline (Elavil), and ergotamine preparations with belladonna alkaloids and phenobarbital. These all have significant side effects such as sedation, loss of energy and drive, dry mouth, constipation, weight gain and gastrointestinal cramping and distress. For symptomatic treatment, ergotamine with caffeine (Cafergot) is commonly used. Other medications include isometheptene mucate (Midrin), NSAID's (Motrin, etc.), dihydroergotamine, the newer medication sumitriptan (Imitrex) which has to be injected intramuscularly and a rapidly expanding class of oral triptans including oral sumitriptan, all of which constrict blood vessels throughout the body, including the coronary vessels. When narcotics, such as Fiorinal with codeine are frequently used, additional hazards include the considerable potential for rebound headache and habituation.

Most neurologists regard atypical facial pain as psychogenic and poorly responsive to all forms of medication. Amitriptyline at bed-time and/or various analgesics and narcotics, are commonly used for this condition for extended time periods, often for decades.

Other modes of treatment for these conditions include: (a) acupuncture, (b) biofeedback, and (c) chiropractic. Acupuncture and chiropractic have been used for headache relief, but studies have failed to show that treatment is much more effective than placebo. Acupuncture requires a highly trained acupuncturist. Biofeedback-training in muscular relaxation may be helpful for muscle contraction headache in selected individuals, but controlled studies have not demonstrated success in the above conditions. It is also very time consuming, requiring many treatments. The applicant herein has described the application of low power lasers to the treatment of various conditions including those referred to herein in U.S. Pat. No. 5,514,168. The treatment therein described involves low power of a very different magnitude (considerably lower) than contemplated herein.

The etiology of tension-type headaches is currently regarded as unknown, and treatment remains non-specific.

Pharmacologic agents such as NSAID'S , antidepressant compounds (tricyclics or MAO inhibitors) and prophylactic anti-migraine drugs have been used. Behavioral treatments such as bio-feedback have provided some relief for some patients. Strategies for coping with stress and physical therapy however, have limited use in certain patients.

Tension-type headache was formerly described as muscle contraction headache. It is of uncertain pathogenesis but some kind of mental or muscular tension may play a causative role. Tension-type headaches fall into two classifications: episodic and chronic. The diagnostic criteria for episodic tension -type headache are: (1) At least 10 previous headache episodes fulfilling the following criteria and the number of days with such headache, less than 180/year. (2) Headache lasting from 30 minutes to 7 days. (3) At least two of the following pain characteristics: pressure/tightening (nonpulsating) quality; mild or moderate intensity may inhibit, but does not prohibit activities; bilateral location; not aggravated by walking stairs or similar routine physical activity. (4) Both of the following must be present: no nausea and vomiting. Photophobia and phonophobia are absent in this condition.

The diagnostic criteria for chronic-type tension headache are that headache frequency is equal to or greater than, 15 days per month or 180 days per year. The characteristic of the headache are similar to that of episodic tension-type headache except that nausea can be accepted as an isolated associated symptom. Our research has indicated that tension-type headaches have a similar etiology to the other painful conditions noted in this specification.

The post-traumatic syndrome, also called post-concussion syndrome, is a constellation of symptoms which can follow mild to moderate closed head injury (actual cranial impact). It can also occur following flexion/extension trauma (whiplash), in which no actual cranial contact has occurred. The primary symptoms include one or more of the following: (1) headache, neck, and shoulder pain, (2) sleep disturbances, (3) cognitive abnormalities, (4) mood and personality changes, including depression, and (5) dizziness.

Headache often persisting for long periods of time, represents the most common symptom in patients with closed head injury. Since the head and cervical spine are functionally interrelated, the cervical spine is usually involved, even if, as in closed head injury, the cervical spine was not injured. Because laser treatment to the intra-oral inflamed area reduces cervical muscle spasm, this may explain why this treatment is particularly effective for post-traumatic headache.

Treatment of acute post-traumatic headache is part of the general management of the cerebral concussion syndrome; physical and mental rest and simple analgesics or anti-inflammatory drugs. Treatment of chronic post-traumatic headache is difficult because of the complex interrelation between organic and psychosocial factors. Daily consumption of analgesics can lead to chronic drug-induced headaches. Behavioral treatments such as biofeedback have limited use. Patients are often treated with antidepressants .

Atypical facial pain falls within an ill-defined category which includes a number of atypical oral pain syndromes. All are characterized by chronic pain, usually constant, but often of varying intensities. Atypical facial pain is relatively constant, mostly unilateral, and unrelated to jaw function. These patients in an attempt to obtain pain relief often undergo irreversible dental changes including root canal therapy and multiple extractions with no appreciable benefits. They respond poorly to all forms of treatment. The pain is not triggered by remote stimuli, but may be intensified by stimulation of the painful area itself There is no identified uniform etiology of atypical oral and facial pain, although it sometimes occurs after dental treatment. Vascular changes have been postulated as an underlying mechanism for atypical facial pain. While various treatment modalities are used for atypical oral and facial pain, surgical or dental intervention should not be undertaken, since such interventions usually are ineffective. Counseling and the use of antidepressants or tricyclics is the present mode of treatment The need for a more appropriate method of treating migraine, tension -type headache, post-traumatic headache, atypical facial pain, and cervical pain and muscle spasm is apparent; the previous methods having often proved ineffective. Treatment with pharmacologic agents is associated with toxicity and must be used systemically. These agents do not meet with patient acceptance or compliance; additionally their administration is often required for many years. Migraine headaches as well as the other conditions treated represent a tremendous economic loss, considering the number of individuals afflicted, the time lost from work as well as the inability to enjoy a normal pain-free life.

SUMMARY OF THE INVENTION

This invention discloses a method for treating migraine, post-traumatic headaches, tension-type headaches, atypical facial pain, cervical pain, and muscle spasm and in some instances, cases of craniofacial neuralgia. involving the application of low power laser beam bursts of energy. The term low level or low power, in this application, is used to define lasers that produce no macroscopic tissue changes and no measurable heat. This application appears particularly effective intra-orally, because the nerves involved in the instant method lie close to the surface and are not protected by skin or bone. They are covered only by a thin layer of mucous membrane.

Laser light has unique properties that enable transmission of high amounts of energy to narrowly defined sites. Biological effects may be thermal, biochemical or mechanical. These effects are governed by tissue optical and thermal properties and laser variables; contact/non-contact, focus, out put power (mW) exposure time (s), and number of exposures. The laser medium governs the wave length emitted.

The Helium-Neon (He—Ne) laser emits at 632.8 nm and is the most commonly used laser in medicine and dentistry. A conventional low-powered Helium-Neon laser is basically a tube filled with helium and neon. When the mixture is stimulated electrically to emission levels, a beam of light in the visible spectrum is emitted. The beam is monochromatic, coherent (relative to wave length and form), and non-divergent. Helium-Neon laser treatment has been used successfully, for treating anatomical sites of the oral mucosa for oral pain (mucositis) in patients receiving high dose chemotherapy Such treatment is well tolerated, feasible, easy to implement and reduces high dose chemotherapy induced oral mucositis, oral pain and requirements for narcotics and parenteral nutrition. He—Ne low-level radiation has been used in treatment of temporomandibular joint pain, trigeminal neuralgia, facial and muscular pain, etc. Results confirm that low level laser treatment is an effective tool, with no side effects and is beneficial for the treatment of many disorders of the maxillofacial region.

Argon laser (488/15 nm) light can also be transmitted through flexible quartz fibers. This laser is useful in dermatology, eye surgery, treatment of glaucoma and in otoscelrossis for small fenestra stapedotomy.

Gallium Arsenide GaAs) (635 nm) and Gallium Aluminum Arsenide (GaMAs) (830 nm) -Crystal lasers can be made from Gallium Arsenide, Lead Telluride, Aluminum and other semi-conductor materials. Because these materials can carry an electric current, electrical pumping of semi-conductor lasers is possible. Such lasers are called diode lasers and are very efficient and small, relative to other types of lasers.

Gallium-Arsenide laser, a low level diode laser, is often used in pain reduction therapy.

Gallium-Aluminum-Arsenide another low level diode laser is a semi-conductor, continuous wave laser. These semi-conductor continuous wave lasers are useful in reducing pain. This palm-size laser source, the preferred embodiment for use herein, incorporates a compact, rugged, laser diode, operating at low voltage, in contrast to the larger Helium—Neon gas lasers, utilizing high voltage electronics, and long gas-filled tubes. This laser diode is a Gallium Arsenide (GaAs) solid state semiconductor device, emitting laser light with a wave length of 635 nm, close to the above He—Ne 632.8 nm laser and an orange-red color. The diode is operated through low powered electronic circuitry, utilizing internal optical feedback to maintain constant power output of 11 mW (less after light passes through the fiber optic and disposable plastic sheath. The disposable sheath is applied for sterility during intra-oral use.)

In this (and the above He—Ne laser), the coherent laser light is focused by lenses into a glass fiber optic assembly. This assembly is attached via a connector to the laser source for convenience and interchangeability. Fiber optics utilize internal reflection through differences of index of refraction of the core and cladding materials for low loss light transmission. The flexible fiber optic structure allows application of laser light at the therapeutic site with a compact easily maneuverable hand-held tip.

For the purposes of this invention, the Helium—Neon laser and the Gallium Arsenide and Gallium Aluminum Arsenide diode lasers are preferred.

The application of laser radiation in all of the procedures described herein can be carried out with the conventional apparatus such as a HeNe-laser as for example a so-called low-power cold laser or soft laser used for treatment in various areas such as rheumatology, dermatology, neurology and in dental medicine. The application of laser radiation in all of the procedures carried out with the above apparatus can also be done with low level diode lasers such as the GaAs or the GaAlAs semiconductor type laser.

Early far field trigeminal somatosensory evoked potentials, with the small stimuli (He—Ne laser) applied over the infraorbital foramen, were used to evaluate low level laser application to nerves unprotected by skin or bone. Twelve healthy adult volunteers received 180 s irradiation to the left maxillary third molar apical area with a Helium-:Neon laser (1.7 mW, 632.5 nm, 50 Hz), resulting in an immediate somatosensory evoked potential amplitude decrease of 61%, and 65.2% and 71.8% decrease ten and twenty minutes later, respectively. In twelve patients used as placebo control, the laser was not plugged in; and there was no amplitude decrease[1.]
[1]Experiment was performed with Arthur Nelson, PT, PhD, founder and Director, Doctoral Program in Pathokinesiology, New York University, 1973–1994, and Professor and Chairman, Dept. of Physical Therapy, New York University, 1970–1983.

Recent research has further implicated the previously described maxillary tender zone as closely related to migraine, tension-type headache, facial pain, and cervical pain and muscle spasm. In a multicenter hospital-based study of 40 patients during unilateral migraine or tension-type headache, the intra-oral maxillary areas were palpated bilaterally, and local temperature measurements were obtained bilaterally. A statistically significantly correlation was found between symptom severity and laterality to laterality and degree of intra-oral tenderness, and between laterality of symptoms to temperature differential.[2]
[2]Friedman M H, Luque F A, Larsen E A, Headache Quarterly—1997.

In an open-label study in the emergency department of a major medical center associated with a medical school, eight physicians treated 25 acute migraine and tension-type headache patients, by chilling the intra-oral tender zones for 40 minutes, using hollow metal tubes, filled with circulating ice water, applied specifically to the maxillary intra-oral zones. Pain relief both immediate and 24 hours later, was significantly better than that routinely obtained in the emergency department with intravenous narcotics.[3]
[3]Friedman M H, Nehrbauer N J, Larsen E A, Headache Quarterly—1999

In an ongoing randomized controlled migraine study in the Department of Medicine at New York Medical College, thirty symptomatic migraine patients were treated by the above intra-oral chilling, bogus (tongue) chilling or 50 mg of oral Sumatriptan, a widely prescribed migraine medication. The pain and nausea relief by intra-oral chilling was statistically significant, as compared to the above noted methods.

When the same technique was used, for only 15 minutes on 12 patients, with cervical pain and muscle spasm, in 9 of these patients, reduced cervical pain perception, upper trapezius electromyography signal reduction, and increased cervical range of motion were obtained. Six out of 12 of these individuals also had accompanying headache, which was reduced or eliminated in four cases.[4]
[4]Friedman M H, Nelson A J. J Orthop Sports Phys Ther—1996

In 30 facial pain patients, the maxillary tender area on the symptomatic side was treated with low-level Helium-Neon laser. Immediate pain resolution was obtained in all patients, and lasting relief from repetitive treatment occurred in 22 patients.[5]
[5]Friedman M H, Weintraub M I, Fonnan S, Am J Pain Man—1994

BRIEF DESCRIPTION OF THE DRAWINGS

This invention will be further explained with reference to the drawings wherein.

DETAILED DESCRIPTION OF THE DRAWINGS

Figure 1:
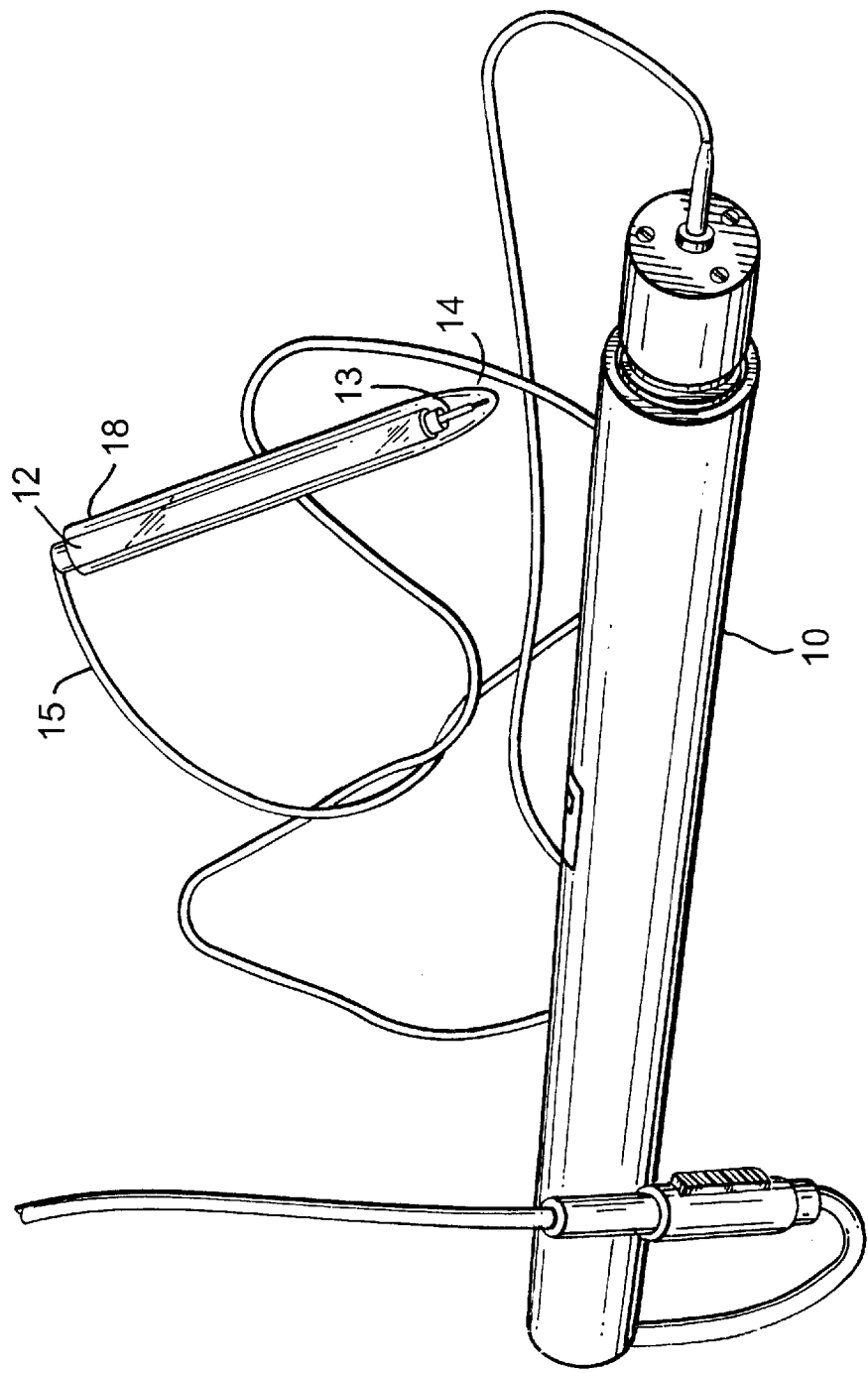
FIG. 1 is a perspective view of a laser apparatus suitable for use in the invention.

The laser illustrated in FIG. 1 is a conventional low-power Helium—Neon laser—a tube filled with helium and neon. When this mixture is stimulated electrically to emission levels, a beam of light in the visible spectrum Oust below infrared) with a wave length of 632.8 nanometers is emitted and allowed to flow through a handheld fiber optic tube for ease of application. The beam is monochromatic, coherent (relative to wave length and form), and non-divergent. The laser 10 in FIG. 1 is powered by normal 110V current and has a maximum output of 15 mW. In FIG. 1, 15 represents the fiber optic tube. There is a disposable inner plastic tube 12 provided with an outer non sterile plastic covering 18 surrounding the optic tube 15 at the point of contact with the patient. As the energy goes through the fiber optic tube 15 it is reduced to 7 mW at the probe tube 13 which is to be applied to a local point, i.e., the area of tenderness of the patient for treatment. The flexible hand piece delivery system is shown in FIG. 1 wherein 15 designates the optic tube and 13 is a metal delivery tube. The delivery tip is comprised of two metal tubes 13 and 14 soldered together. The fiber optic tube goes through both of them. The small tube, in addition to allowing the laser beam to issue forth, serves as a tool to record tender areas when it is pressed against the gingiva.

Figure 2:
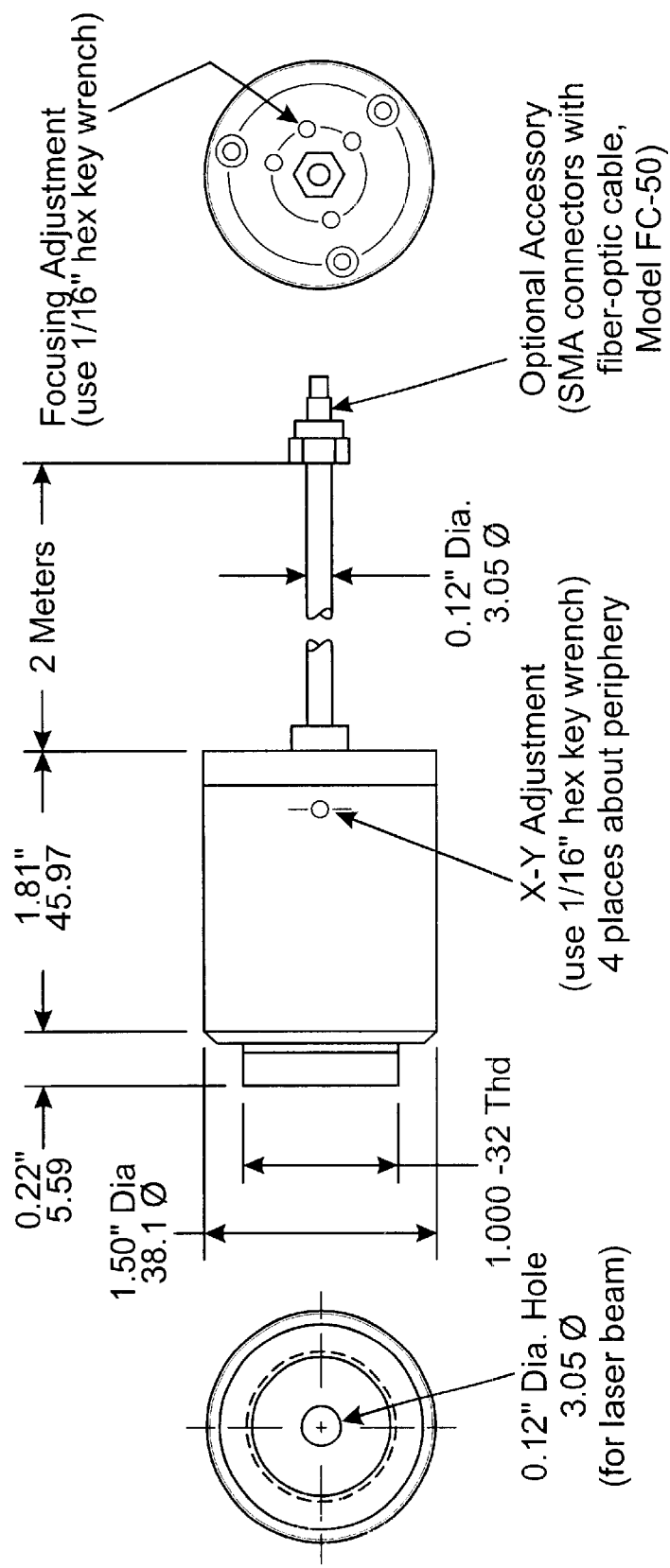
FIG. 2 is a schematic illustration of the coupling of a helium—neon laser to a fiber optic cable.

The fiber optic cable and its coupling with the helium—neon laser can be seen in FIGS. 2. The fiber optic adapter efficiently couples a helium—neon laser to a fiber-optic cable. The fiber-optic attachment contains optics and a positioning system to focus the laser beam. Once the fiber is attached, precision alignment in Z directions may be performed with the set screws. The Z alignment permits maximum fiber transmission by focusing the beam diameter at the point the fiber connects to the fiber optic adapter. The fiber optic adapter will couple to any laser equipped with a 1"-32 thread, and will work with any fiber with an adapter assembly type connector. The fiber optic adapter is constructed of black anodized aluminum and weighs 0.4 pounds (0.18 kg). The fiber optic cable is a 6 foot (2 m) long stepped multimode fiber with 50 micron core diameter.

Figure 3:
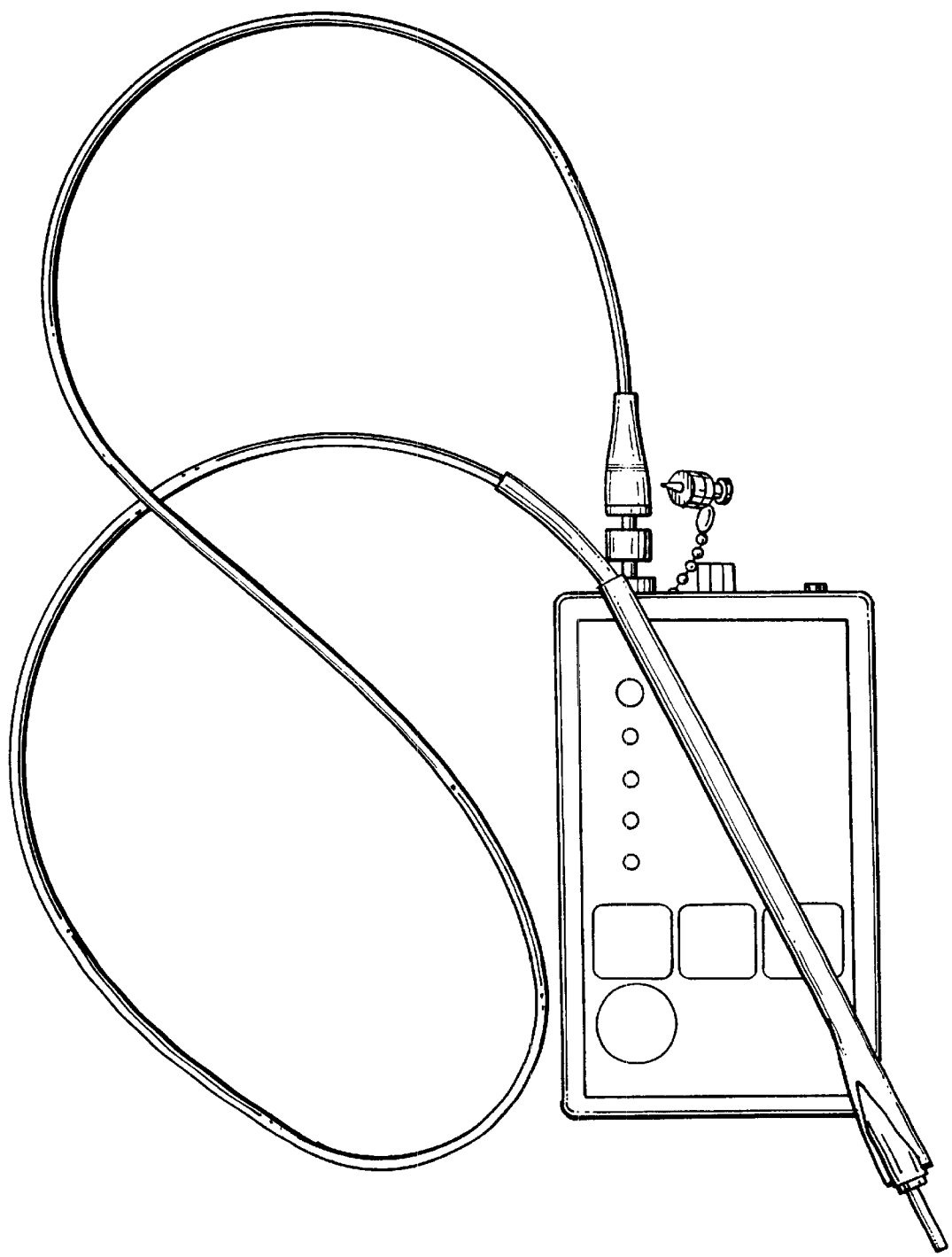
FIG. 3 illustrates a diode laser and a new flexible disposable saliva ejector delivery system suitable for use in the invention.

FIG. 3 illustrates a flexible plastic delivery system attached to a laser diode for use in the invention. The application corresponds to that shown in FIG. 1.

Figure 4:
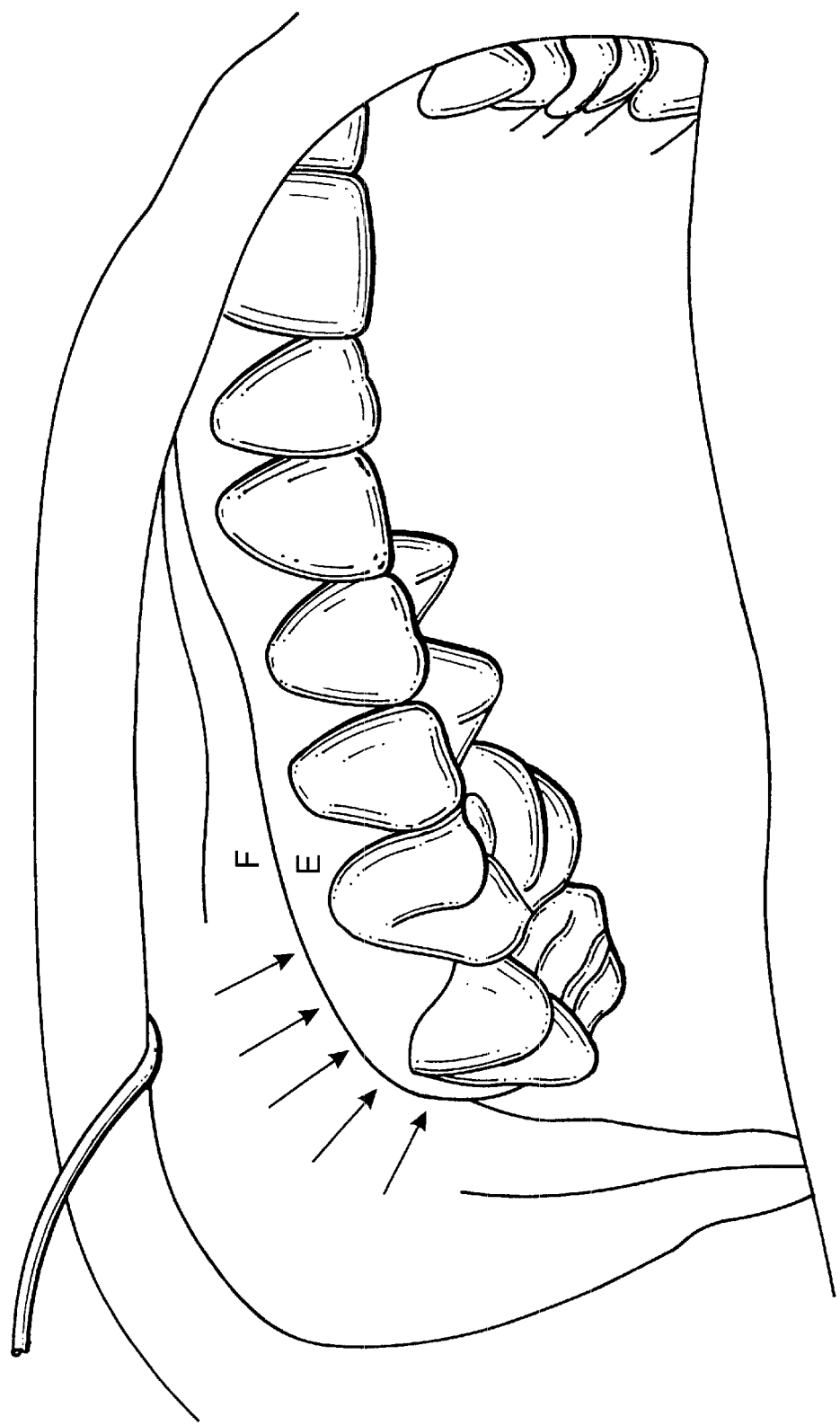
FIG. 4 illustrates the location of the maxillary zone of tenderness intra-orally.

FIG. 4 illustrates the location of the intra-oral zone of maxillary tenderness of one side of the face. The arrows represent the zone of tenderness. E designates the attached gingiva and F the alveolar mucosa.

The human nervous system has been demonstrated to be photosensitive, and therapeutic effects relative to pain and wound healing have been reported for the low power laser. Prolonged direct viewing of the laser beam may injure the eye, and patients who are photosensitive probably should not have laser therapy. However, even at doses 75 times that described below, untoward side effects from low level laser therapy have not been reported.

An intra-oral zone of tenderness is present over the root apical areas of the posterior maxillary teeth in over 93% of patients with migraine, tension-type headache, cervical muscle spasm, post-traumatic headache, and atypical facial pain. This focal tenderness is located on the symptomatic side (bilateral if symptoms are bilateral), and is present even when the patient is symptom free. The area does not represent dental pathology, is radiographically negative, and is not usually noticed by the patient or dentist because of its inaccessibility. The area, usually more tender at its posterior aspect, is located around a nerve plexus formed by the posterior superior alveolar branch of the maxillary nerve (FIG. 4). FIG. 4 illustrates the location of the intra-oral zone of maxillary tenderness of one side of the face. The arrow represent the zone of tenderness, A designates the gingiva and B the alveolar mucosa. The posterior alveolar nerves (left and right) arise from the maxillary nerve (the second division of the trigeminal (V) nerve) and descend to form the plexus above the root apices of maxillary molar teeth. The middle superior alveolar nerves supply the premolar teeth, and occasionally contribute to this plexus.

In order to demonstrate the safety and efficacy of the method of the invention, an investigation was carried out using a large number of patients. Using groups of patients with migraine (65) and facial pain (35), 59 of the migraine patients (92%) and all of the facial pain patients (100%) experienced an immediate elimination or significant reduction of maxillary apical tenderness from brief, (30 to 120 second) applications of low level (non-cutting laser). A 15 mW helium—neon laser emitting approximately 7 mW through the fiber-optic and plastic sheath was used. In another group of 20 migraine patients, the same results were achieved in 18 patients (90%) using 60 second bursts from a 5 mW laser diode.

The protocol for treatment of a group of 42 patients with atypical facial pain was as follows: A 30–540 second application of low-power laser (7 mW helium-neon) to the intra-oral zone of tenderness (FIG. 4) located on the symptomatic side was used. This was significantly longer and the laser was more powerful than in the inventor's earlier U.S. Pat. No. 5,514,168 because of the consistent clinical observation that greater exposures are far more efficient. In order to insure sterility, the laser tip was encased in a disposable thin plastic dental hand piece cover, and light tissue contact with laser tip was maintained. The above procedure was followed for each subsequent visit. In most cases, reoccurrence or partial reoccurrence of pain and tenderness was reported at the return visit, four to seven days later. To eliminate facial pain, the majority of patients required from one to four additional treatments.

The above treatment is identical for that utilized with migraine patients, but may require more visits, averaging approximately seven treatments, over a longer period of time for headache patients.

In connection with the above treatment, additional laser treatment can be extended to the four foramina, i.e., the supraorbital, infraorbital, mandibular, and mental, where the supraorbital, mandibular, buccal, and mental nerves lie close to the surface (direct laser contact using similar doses as previously described, 30–540 seconds of 7 mW He—Ne laser). Similar exposures with a 5 mW laser diode can be used. Direct laser application reduces or eliminates symptoms by reducing hyperexcitability of the affected nerves. The supraorbital foramen was exposed to the laser for frontal (tension) or vascular headache and anodynia (eye pain) often related to these headaches. The sensory (supraorbital) nerve to the eye and forehead exits at the junction of the medial and middle third of the supraorbital ridge Oust under the eyebrow) and is extremely accessible to the laser. The location of the infraorbital foramen makes it readily accessible to the laser. The mandibular and mental foramen were exposed to the laser in facial pain patients where symptoms involved the lower jaw.

The results obtained by treating patients with atypical facial pain and vascular headaches follow:

Of the 42 facial pain patients, 32 experienced complete elimination of pain, the results were partially successful in 6 and 4 failed to obtain relief Some of the partially successful subjects required additional widely-spaced treatments to maintain symptomatic relief.

Of the 108 migraine patients, 86 (83%) experienced elimination or significant reduction in headache frequency and/or intensity. Of these migraine patients, 85% were taking medication. Of the successful patients over 90% of those taking medication were able to significantly reduce or eliminate their medication. Of the 37 tension-type headache patients, 30 (81%) were successful. These figures were arrived at after two to ten weeks of treatment (from two to eight visits). Similar to some of the facial pain patients, many of the successful headache patients required additional widely spaced treatment to maintain relief. Headache patients with cervical dysfunction were accepted for treatment; with physical therapy prescribed for the majority of them.

Side effects have not been observed in the above patients, nor have any been reported in the literature for other conditions even with more lengthy exposures and with much more powerful lasers up to 75 mW with HeNe and 200 mW with diode lasers.

A protocol, utilizing the HeNe laser for treatment of migraine, post-traumatic headache, atypical facial pain, tension-type headaches cervical pain, and muscle spasm and in some instances cranio-facial neuralgias using high doses (mW) was followed in order to shorten treatment time as well as to decrease the number of treatments necessary for elimination of symptoms. In previous protocols, the treated sites were irradiated with 7 mW for a total of 15 minutes— 7.5 minutes on each side. Such regimens resulted in post-traumatic headache reduction and lessening or elimination of cervical pain in most cases. Using a laser capable of emitting doses up to 60 mW, doses of low level laser radiation of from 4 mW to 200 mW with exposure times of 3 to 8 minutes applied to the intra-oral zone of tenderness and in some instances additional treatment was extended to include radiation to the (foramina, the supraorbital, infraorbital, mandibular).

Treatment with other low-level lasers, in particular the semi-conductor diode lasers, GaAs (635 nm) has also been effective in the above conditions.

Twenty six patients were treated with GaAs (635 nm) laser radiation for a total of 5 mW, 300 seconds for one applications per week. At the end of the treatment period of the 26 patients 13 were asymptomatic, 7 improved considerably and 6 remained symptomatic. Results indicate that the diode laser is effective in treatment of the above conditions.

Treatment with low level laser light as described above has substantially reduced the pain and other symptoms associated with the above disorders as well as improved the quality of life of these patients.

I claim:

1. A method of treating migraine, tension-type headache, post-traumatic headache, cervical pain, muscle spasm and atypical facial pain which comprises generating successive pulses of laser radiation utilizing a pulsed Helium-Neon. Gallium Arsenide or Gallium Aluminum Arsenide laser including optical fiber means connected to said laser for guidingy said laser radiation out from said laser to the location to be treated comprising an intra-oral area of maxillary tenderness formed by the branches of the maxillary nerve, said optical fiber means terminating in an application probe tip and said laser having a radiation output of about 4 to about 200 mW, placing said probe tip into the mouth of a subject suffering from said condition adjacent to the area of tenderness associated with the plexus formed by the posterior and middle superior alveolar branches of the ipsi lateral maxillary nerve, producing successive pulses of radiation through said optical fiber means and probe tip so that the radiation impinges on said plexus to at least reduce the subject's symptoms, wherein the treatment with pulses of radiation has a duration of 2–15 minutes and said applications are made to said zone of tenderness from proximal to distal in 2–3 mm increments.

2. Method according to claim 1 wherein said subject suffers from migraine headache.

3. Method according to claim 1 wherein said subject suffers from atypical facial pain.

4. Method according to claim 1 wherein the treatment with pulses of radiation is applied bilaterally and has a duration of up to 9 minutes on each side.

5. Method according to claim 1 wherein said laser is a He—Ne laser and has a maximum output of about 75 mW.

6. Method according to claim 1 wherein said laser is a Gallium Arsenide laser.

7. Method according to claim 1 wherein said laser is a Gallium Aluminum Arsenide laser.

8. Method according to claim 1 wherein said laser is a helium—neon laser and has an output of about 5 to about 60 mW.

9. Method according to claim 1 wherein said laser is a gallium Aluminum laser or gallium Arsenide laser and has a maximum output of about 200 mW.

10. Method according to claim 1 wherein said treatment is repeated at spaced intervals to eliminate the pain.

11. Method according to claim 1 wherein said subject suffers from post-traumatic headache pain.

12. Method according to claim 1 wherein said subject suffers from cervical pain.

13. Method according to claim 1 wherein said subject suffers from cervical muscle spasm.

14. Method according to claim 1 wherein said subject suffers from tension type headache.

15. Method according to claim 1 wherein said subject suffers from migraine headache.

16. A method of treating migraine. tension-type headache, post-traumatic headache, cervical pain, muscle spasm and atypical facial pain which comprises generating successive pulses in laser radiation utilizing a pulsed Gallium Arsenide or Gallium Aluminum Arsenide laser including optical fiber means connected to said laser for guiding said laser radiation out from said laser to the location to be treated comprising an intra-oral area of maxillary tenderness formed by the branches of the maxillary nerve, said optical fiber means terminating in an application probe tip and said laser having a radiation output of about 4 to about 200 mW, placing said probe tip into the mouth of a subject suffering from said condition adjacent to the area of tenderness associated with the plexus formed by the posterior and middle superior alveolar branches of the ipsi lateral maxillary nerve, producing successive pulses of plexus to at least reduce the subject's symptoms, wherein the treatment with pulses of radiation has a duration of 2–15 minutes and said applications are made to said zone of tenderness from proximal to distal in 2–3 mm increments.

* * * * *